(12) United States Patent
Hagan et al.

(10) Patent No.: US 8,773,656 B2
(45) Date of Patent: Jul. 8, 2014

(54) APPARATUS AND METHOD FOR CHARACTERIZING GLASS SHEETS

(75) Inventors: Richard Hagan, Manville, NJ (US);
Michael Albert Joseph, II, Corning, NY (US); Philip Robert LeBlanc, Corning, NY (US)

(73) Assignee: Corning Incorporated, Corning, NY (US)

( * ) Notice: Subject to any disclaimer, the term of this patent is extended or adjusted under 35 U.S.C. 154(b) by 105 days.

(21) Appl. No.: 13/591,994

(22) Filed: Aug. 22, 2012

(65) Prior Publication Data
US 2013/0067956 A1    Mar. 21, 2013

Related U.S. Application Data

(60) Provisional application No. 61/526,860, filed on Aug. 24, 2011.

(51) Int. Cl.
*G01N 23/00* (2006.01)
*G01N 21/896* (2006.01)
*G01N 21/958* (2006.01)
*G01N 21/01* (2006.01)

(52) U.S. Cl.
USPC ............. 356/239.1; 356/239.2; 356/239.7; 356/239.8; 65/29.12; 65/29.18

(58) Field of Classification Search
CPC ..... G01N 33/386; G01N 21/86; G01N 21/88; G01N 21/89; G01N 21/8914; G01N 21/896; C03B 35/205; C03B 2225/02; C03B 35/207
USPC ............. 356/239.1, 239.2, 239.7, 239.8; 65/29.12, 29.14, 29.18
See application file for complete search history.

(56) References Cited

U.S. PATENT DOCUMENTS

| | | | | |
|---|---|---|---|---|
| 3,062,520 A | * | 11/1962 | Frey et al. | 432/5 |
| 3,666,084 A | * | 5/1972 | Stehl | 198/866 |
| 4,824,248 A | * | 4/1989 | Neumann | 356/244 |
| 5,587,796 A | * | 12/1996 | Rakitsch et al. | 356/445 |
| 5,642,189 A | * | 6/1997 | Alguard | 356/72 |
| 5,642,192 A | * | 6/1997 | Gordon et al. | 356/328 |
| 5,654,799 A | * | 8/1997 | Chase et al. | 356/600 |
| 5,793,486 A | * | 8/1998 | Gordon et al. | 356/328 |
| 6,588,118 B2 | * | 7/2003 | Hellstrom | 33/501.02 |
| 7,077,019 B2 | * | 7/2006 | Weiss et al. | 73/865.8 |

(Continued)

OTHER PUBLICATIONS www.newwayairbearings.com.

*Primary Examiner* — Jason L Lazorcik
(74) *Attorney, Agent, or Firm* — Kevin M. Able

(57) ABSTRACT

Disclosed is an apparatus for characterizing attributes of a moving glass sheet comprising complementary mechanical material handling technologies that progressively stabilize, position, capture, flatten, and release the lower portion of glass sheets traveling past the apparatus while posing minimal constraint on the top section of the sheet. The apparatus includes a pressure-vacuum (PV)-type device comprising distinct regions such that the glass sheets experience a non-contact but gradual increase in constraining force until the point where measurements can be performed, then a gradual decrease in constraining force until the glass sheets are released from the inspection station. This graduated force technique is applied along the direction of travel of the sheets and may also be applied vertically upwards along the height of the sheet to restrict the motion of the sheet without constraining it at pinch points near the conveyor.

11 Claims, 13 Drawing Sheets

(56) References Cited

U.S. PATENT DOCUMENTS

| | | | |
|---|---|---|---|
| 7,137,309 B2* | 11/2006 | Weiss et al. | 73/865.8 |
| 7,567,344 B2* | 7/2009 | LeBlanc et al. | 356/239.1 |
| 7,889,342 B2* | 2/2011 | Hellstrom et al. | 356/429 |
| 8,393,460 B2* | 3/2013 | Koizumi et al. | 198/617 |
| 2005/0040338 A1* | 2/2005 | Weiss et al. | 250/358.1 |
| 2006/0096395 A1* | 5/2006 | Weiss et al. | 73/865.9 |
| 2008/0174771 A1* | 7/2008 | Yan et al. | 356/237.5 |
| 2008/0229811 A1* | 9/2008 | Zhao et al. | 73/104 |
| 2009/0028423 A1 | 1/2009 | Sandstrom et al. | 382/149 |
| 2011/0069306 A1* | 3/2011 | Doyle et al. | 356/237.5 |
| 2012/0062877 A1* | 3/2012 | Doyle et al. | 356/237.5 |

* cited by examiner

APPARATUS AND METHOD FOR CHARACTERIZING GLASS SHEETS

This application claims the benefit of priority under 35 U.S.C. §119 of U.S. Provisional Application Ser. No. 61/526,860 filed on Aug. 24, 2011 the content of which is relied upon and incorporated herein by reference in its entirety.

BACKGROUND

1. Field

The present invention relates to an apparatus and method for characterizing glass sheets, and in particular to an apparatus adapted to measure one or more selected attributes of a glass sheet while the glass sheet is in motion.

2. Technical Background

The invention relates to controlling motion and attitude of a glass sheet being conveyed along a predetermined path to enable high resolution online measurements, such as topography inspection (e.g. nanotopography, or topography on a nanometer scale). Accurate online measurements of thin glass sheets, and in particular the measurement of nanometer-scale features, is highly dependent upon consistently presenting the glass sheets in a predetermined plane at a predetermined orientation and eliminating the vast majority of vibrations and oscillations of the glass. Challenges such as high accuracy measurement of thickness, waviness, and cord are highly dependent on presenting the glass surface to measurement gauges with reproducible, high tolerance material handling.

Online process control and quality measurements, such as online cord and streak inspection, suffer from a lack of repeatability when performed while simply gripping the glass in a non-quality area. A large part of the material presentation challenge is keeping the sheet of glass moving down a production line while being suspended from a carrier on an overhead conveyor. This constraint often forces measurements to be performed either in a separate inspection portion of the process line, completely offline, or the measurement technology compatible with coarse traditional online material handling is limited in its performance (e.g. resolution).

High resolution metrology is performed online in other industries, such as silicon wafers or paper and plastic webs, but in these cases, the product is in direct contact with a supporting plate, as with wafers, or with rollers, as with most webs. The size and contact prohibition on glass sheets suitable for display applications presents a difficult challenge for handling.

SUMMARY

Measurement of thin glass sheets, generally equal to or less than 1 mm in thickness, may exhibit an amount of curvature or warping that creates difficulty when measuring certain attributes of the glass, particularly if the glass is large (e.g. greater than about 4 m$^2$). To overcome this deficiency, the glass must first be flattened. In the past, flattening and stabilizing the glass sheet has involved removing the sheet from the inline path, transferring the glass sheet to a precision granite base, then vacuuming individual glass sheets to a vacuum table, making the desired measurements, removing the glass sheets, and then performing the same operation with another glass sheet. Such a piecemeal approach adds considerable time and expense to a manufacturing process. The challenge of measuring large thin glass sheets is exacerbated if there is a need to measure the glass sheet while the glass sheet is transported along a manufacturing line.

In some manufacturing processes, glass sheets can be conveyed from one location to another location by clamping the glass sheet to a moving member in an overhead conveyor. It would be beneficial if one or more of the aforementioned characterizations could be accomplished while the glass sheet was in motion, without first dismounting the glass sheet and positioning the glass sheet on a measurement table as a stationary object.

To that end, an apparatus is disclosed for making precision measurements of moving glass sheets, such as glass sheets suitable for use in a liquid crystal display devices, by constraining the glass sheets while still held by a conveyor carrier. The material handling features of the apparatus include air knives and pressure-vacuum (PV) air bearings, arranged in linear fashion such that a glass sheet entering the apparatus is subjected to a non-contact but gradual increase in constraining force until the point where measurements can be performed. A gradual decrease in constraining force then occurs until the sheet is released from the apparatus. This graduated force technique is applied along the direction of travel of the glass sheets and also vertically upward along the height of the sheets to restrict the motion of the sheets without constraining it at pinch points near the conveyor carriers.

Accordingly, an air bearing is disclosed comprising an annular inner porous body portion comprising a circular groove in a surface of the inner porous body portion, and a plurality of radial grooves intersecting the circular groove, the inner porous body portion defining a central passage extending through a thickness of the air bearing; an outer porous body portion disposed about the inner porous body portion, wherein the outer porous body portion comprises a plurality of continuous grooves in a surface of the outer porous body portion; and wherein each continuous groove of the outer porous body portion comprises a plurality of vacuum ports. The circular groove of the inner porous body portion and the radial grooves of the inner porous body portion divide the surface of the inner porous body portion into a plurality of sub-surfaces, and a sub-surface of the plurality of sub-surfaces comprises a vacuum port. Preferably, each sub-surface of the plurality of sub-surfaces comprises a vacuum port.

The outer porous body portion preferably comprises an arcuate outer circumference, and preferably the outer porous body portion comprises a circular outer circumference such that the air bearing comprises an annular inner porous body portion and an annular outer porous body portion disposed about and concentric with the inner porous body portion. In some embodiments the air bearing comprises a plurality of inner porous body portions. For example, the plurality of inner porous body portions may be aligned along a horizontal axis.

In another embodiment, an apparatus for characterizing glass sheets as the glass sheets move past the apparatus is disclosed comprising: an air bearing comprising an annular inner porous body portion, and an outer porous body portion disposed about the inner porous body portion, the inner porous body portion defining a central passage extending through a thickness of the air bearing; a plurality of stabilizing air knives positioned upstream of the air bearing relative to a direction of travel of the glass sheets; and a measurement device to measure at least one attribute of the glass sheet, the measurement device being aligned with the central passage of the air bearing. The inner porous body portion comprises a circular groove in a surface thereof. The inner porous body portion may further comprise a plurality of radial grooves intersecting the circular groove. The surface of the inner porous body portion comprises a vacuum port. If the inner porous body portion comprises a circular groove and a plurality of radial grooves, the circular groove and the radial grooves define a plurality of sub-surfaces on the inner porous body portion. Preferably, each sub-surface comprises a vacuum port.

The outer porous body portion comprises a plurality of continuous (i.e. closed) grooves, each continuous groove comprising a plurality of vacuum ports. For example, each continuous groove can be a circular, oval, elliptical, or any other closed, continuous shape. Preferably, an outer circumference of the outer porous body portion is arcuate. For example, the outer circumference of the outer porous body portion may be circular. The air bearing may in some embodiments comprise a plurality of inner porous body portions.

The measurement device preferably measures the at least one attribute through the passage defined by the inner porous body portion.

The stabilizing air knives are oriented such that a flow of air from the stabilizing air knives is angled in a downward direction. That is, the flow of air from the stabilizing air knives is preferably directed in a downward direction relative to a horizontal plane so that the flow of air makes an acute angle with the glass sheet. For example, a direction of the flow of air may form an angle in a range from about 15 degrees to about 75 degrees relative to the glass sheet. Preferably, the stabilizing air knives are arcuate in shape.

The apparatus according to the present embodiment may further comprise a positioning air knife positioned downstream of the air bearing to force the glass sheet in a direction away from the air bearing.

In still another embodiment, a method of characterizing moving glass sheets is described comprising: moving a glass sheet in a first direction along a predetermined path, the glass sheet comprising a pair of opposing major surfaces, a bottom edge, and a leading edge relative to the first direction; dampening movement of the glass sheet in a second direction perpendicular to the first direction by passing the glass sheet between at least two stabilizing air knives as the glass sheet is moving in the first direction; engaging the glass sheet with a circular air bearing, the circular air bearing comprising an inner porous body portion and a outer porous body portion disposed about the inner porous body portion, the inner porous body portion defining a central passage therethrough; and measuring at least one attribute of the glass sheet as the glass sheet moves in the first direction. The method may further comprise guiding a bottom edge of the glass sheet with an edge guiding device comprising guide arms arranged to form a "V"-shaped slot therebetween.

A height of the air bearing, and more particularly a height of the outer porous body portion, is less than one half a height of the glass sheet. The air bearing is positioned such that an upper one half of the glass sheet is preferably not adjacent to the air bearing as the glass sheet is measured. The air bearing is preferably capable of maintaining the glass sheet within +/−15 μm of a predetermined distance from the inner porous body portion.

The first inner porous body portion comprises a circular groove in a surface thereof. The inner porous body portion preferably also comprises a plurality of radial grooves in the surface of the inner porous body portion, wherein the plurality of radial grooves intersect the circular groove.

The outer porous body portion of the air bearing preferably comprises a plurality of concentric grooves, wherein each groove of the plurality of concentric grooves comprising a plurality of vacuum ports.

In still another embodiment, a method of making a glass sheet is described comprising: heating a batch material in a melting furnace to form a molten glass material; flowing the molten glass material over converging forming surfaces of a forming body to produce a glass ribbon; cutting a glass sheet from the glass ribbon; suspending the glass sheet vertically from a conveyor, the conveyor moving the glass sheet in a first direction along a predetermined path; dampening movement of the glass sheet in a second direction perpendicular to the first direction by passing the glass sheet between at least two stabilizing air knives as the glass sheet is moving in the first direction; engaging the glass sheet with an air bearing, the air bearing comprising an annular inner porous body portion and a outer porous body portion disposed about the annular inner porous body portion, the annular inner porous body portion defining a central passage therethrough; and measuring at least one attribute of the glass sheet through the central passage as the glass sheet moves in the first direction. The outer porous body portion preferably comprises an arcuate outer circumference, such as a circular outer circumference.

The inner porous body portion comprises a circular groove in a surface thereof, and further preferably comprises a plurality of radial grooves intersecting the circular groove. The outer porous body portion comprises a plurality of continuous grooves in a surface thereof.

The method may further comprise using a first positioning air knife to move the glass sheet in a direction away from a leading edge of the air bearing. In a further optional step, the method may further comprise using a second positioning air knife to move the glass sheet in a direction toward the air bearing. In still another optional step, the method may further comprise using a third positioning air knife to move the glass sheet away from a trailing edge of the air bearing.

Each stabilizing air knife of the at least two stabilizing air knives directs a flow of air in a downward direction. A leading end of a stabilizing air knife of the at least two stabilizing air knives may optionally be pitched or inclined downward relative to a trailing end of the stabilizing air knife.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and constitute a part of this specification. The drawings illustrate various embodiments of the invention and, together with the description, serve to explain the principles and operations of the invention.

DETAILED DESCRIPTION

Figure 1:
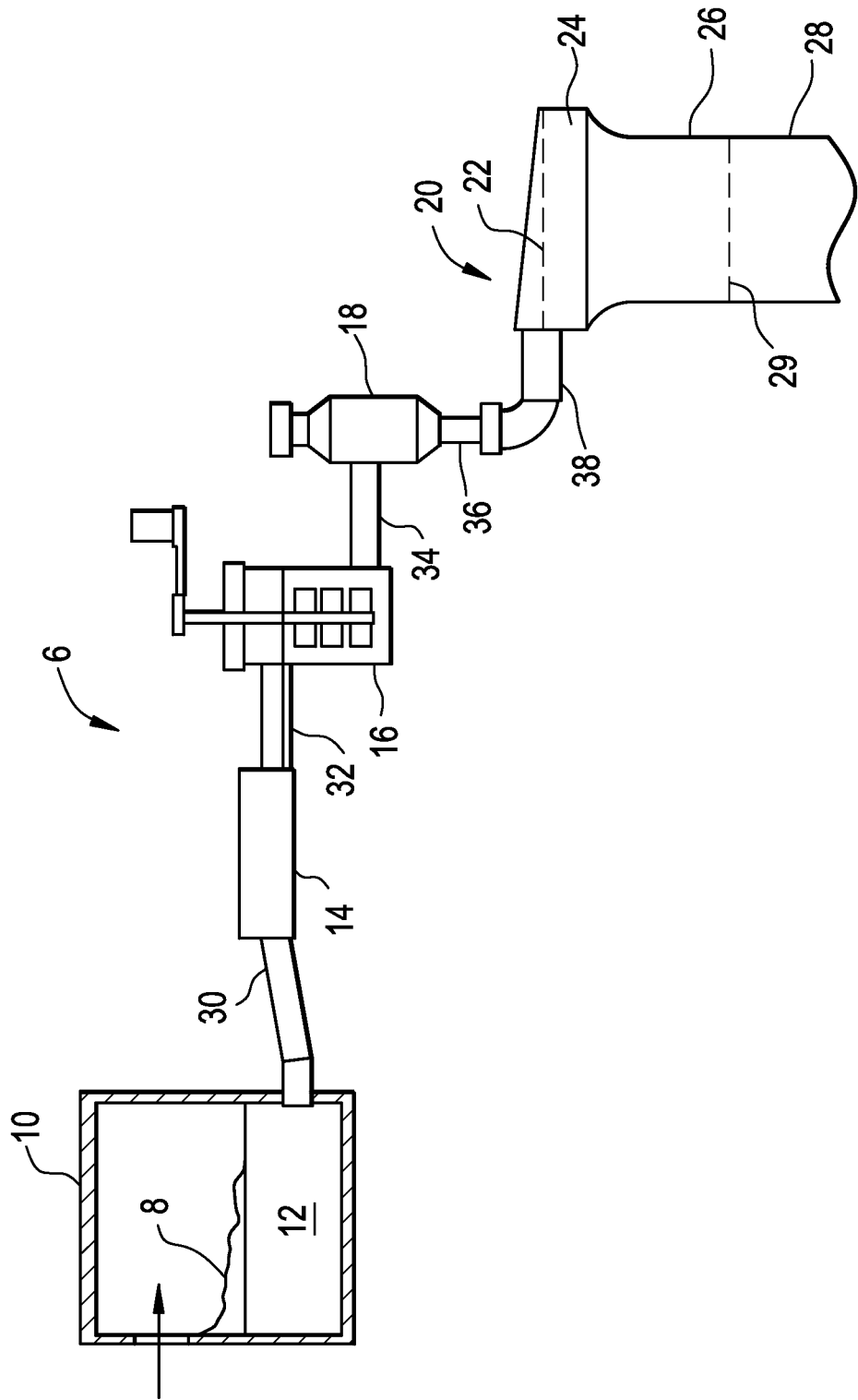
FIG. 1 is a schematic diagram of an exemplary fusion glass making system for producing glass sheets.

In the following detailed description, for purposes of explanation and not limitation, example embodiments disclosing specific details are set forth to provide a thorough understanding of the present invention. However, it will be apparent to one having ordinary skill in the art, having had the benefit of the present disclosure, that the present invention may be practiced in other embodiments that depart from the specific details disclosed herein. Moreover, descriptions of well-known devices, methods and materials may be omitted so as not to obscure the description of the present invention. Finally, wherever applicable, like reference numerals refer to like elements.

In a down draw glass sheet making process, such as a fusion down draw process for example, glass sheets are formed by drawing a viscous glass material vertically downward under suitable conditions of viscosity and draw rate to form a ribbon of glass. The ribbon of glass comprises a viscous liquid at the upper-most extreme position of the ribbon and transitions from a viscous liquid to a solid glass ribbon as the material passes through the glass transition temperature range. When the descending bottom portion of the ribbon has reached a suitable temperature and viscosity, a glass sheet is cut from the ribbon, and so the process continues, with the glass sheets being cut from a continuously descending glass ribbon.

An exemplary fusion down draw glass making system 6 is shown in FIG. 1. In accordance with FIG. 1, batch materials 8 are loaded into melting furnace 10 and heated to form viscous molten glass material 12. Molten glass material 12 is conveyed through finer 14 where bubbles are removed from the molten glass material, and then stirred in stirring apparatus 16 to homogenize the molten glass material. The stirring operation seeks to eliminate variations in the chemical consistency of the molten glass material, thereby avoiding variations in the physical and optical properties of the final glass. Once the molten glass material has been stirred, it flows through receiving vessel 18 and then to forming body 20. Receiving vessel 18 functions as an accumulator by dampening minor flow fluctuations. Forming body 20 comprises a ceramic body having an open channel 22 in an upper portion of the body, and a pair of converging exterior forming surfaces 24 that join at a bottom of the forming body. The molten glass material overflows the open channel of the forming body and flows down the converging forming surfaces of the forming body as two separate flows of molten glass material. The separate flows of molten glass material join and form a single flow or ribbon 26 of material where the converging forming surfaces come together. The ribbon cools as it descends through the glass transition temperature region and forms a solid glass ribbon from which glass sheets 28 are cut along cut line 29.

Melting furnace 10 is connected to and in fluid communication with finer 14 through melter-to-finer connecting tube 30, and finer 14 is connected to and in fluid communication with stirring apparatus 16 through finer-to-stirring apparatus connecting tube 32. Stirring apparatus 16 is connected to and in fluid communication with receiving vessel 18 through stirrer-to-receiving vessel tube 34, and receiving vessel 18 is connected to and in fluid communication with forming body 20 through downcomer tube 36 and forming body inlet 38. While melting furnace 10 is typically formed from a ceramic material, such as ceramic bricks (e.g. alumina or zirconia), those components involved in transporting and processing the molten glass material are typically formed from platinum, or a platinum alloy such as a platinum-rhodium alloy. Thus, melter-to-finer connecting tube 30, finer 14, finer-to-stirring apparatus connecting tube 32, stirring apparatus 16, stirring apparatus-to-receiving vessel tube 34, receiving vessel 18, downcomer tube 36 and forming body inlet 38 typically comprise platinum or a platinum rhodium alloy.

Since the glass sheets begin as vertically oriented sheets when they are removed from glass ribbon 26, reduced handling is possible if the glass sheets can be maintained in a vertical orientation as they are transported through at least a portion of the manufacturing process downstream of the forming process. Thus, in certain manufacturing processes the glass sheet is attached to and supported from a raised conveyor after being cut from the ribbon and moved through at least a portion of the process line in a vertical orientation. In addition, it is more efficient to perform post-forming processing while the glass sheet is traveling rather than dismounting the sheet, placing the sheet in a fixture, processing the sheet, remounting the sheet and transporting it to a subsequent process. To that end, an apparatus is disclosed herein for measuring characteristics of a glass sheet after the sheet has been cut from the ribbon and as the glass sheet is moving. Measured characteristics can include cord, streak or thickness. Cord relates to a compositional inhomogeneity in the bulk glass. This composition inhomogeneity can lead to periodic nanometer-scale topography deviations. In the liquid crystal display (LCD) field, these deviations can lead to periodic cell gap variations in the display panel itself, which in turn lead to contrast streaks to which human perception is finely attuned. Streaks can cause the same distortions in LCD panels but are caused by flow distortions on the body used to form the glass sheet. In accordance with FIG. 2, before entering apparatus 40, the glass sheet is transported by securing the glass sheet only at the upper edge of the glass sheet so that the glass sheet hangs freely from this support.

While the preceding brief description is focused on a fusion down draw glass sheet manufacturing process, the present invention is not limited to a fusion down draw process, and could be practiced in other glass sheet manufacturing processes, such as a slot draw process.

Figure 2:
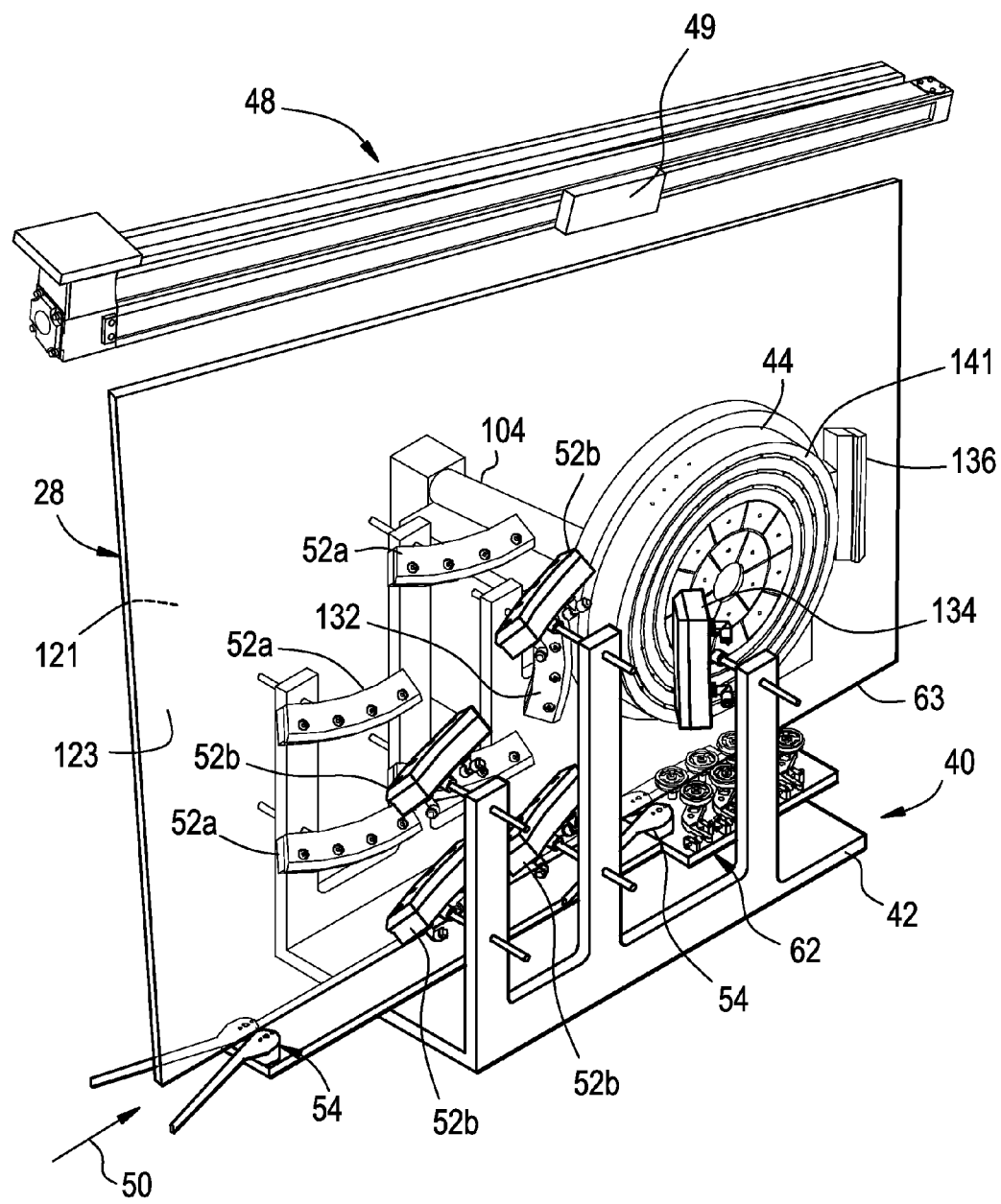
FIG. 2 is a perspective view of an apparatus for characterizing a glass sheet according to an embodiment of the present invention.
Figure 3:
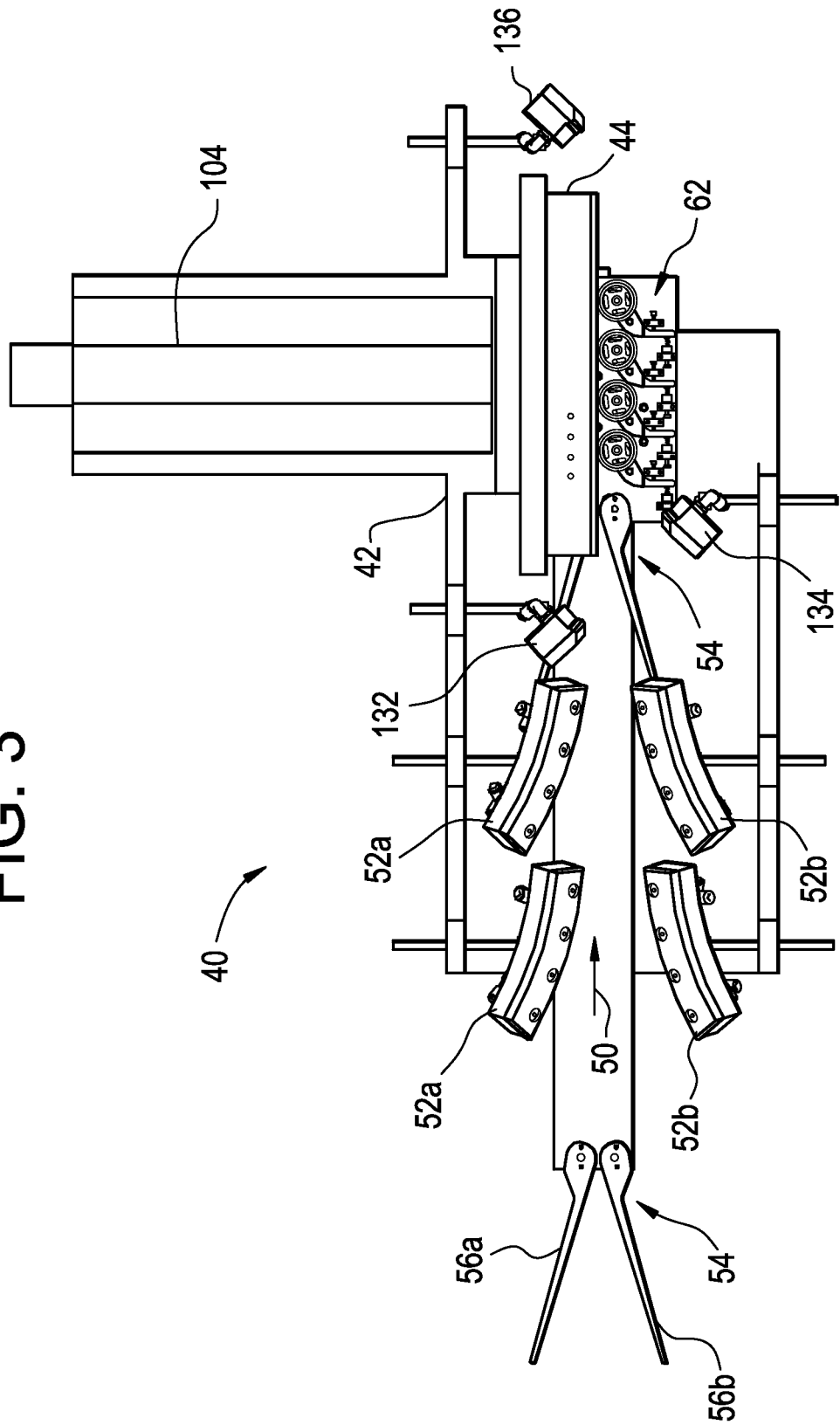
FIG. 3 is a view of the apparatus of FIG. 2 seen looking down on the apparatus.

FIGS. 2 and 3 depict an exemplary embodiment of an apparatus 40 for measuring characteristics of a glass sheet. As shown in both FIGS. 2 and 3, apparatus 40 comprises a frame 42 supporting a circular air bearing 44 in an upright, vertical orientation. Air bearing 44 is a pressure-vacuum device designed to maintain a substrate, such as a glass sheet, at a predetermined distance, and within a maximum deviation, from the surface of the air bearing. The predetermined distance is referred to as the fly height. The fly height represents an equilibrium position of the substrate relative to the air bearing. As air is drawn from between the glass sheet and the air bearing through one or more vacuum ports, ambient air pressure forces the substrate toward the air bearing. However, as the substrate moves toward the air bearing, the force against the substrate produced by the air issuing from the porous surface(s) of the air bearing increases, until the substrate reaches a position where the forces are in equilibrium. Thus, the substrate is captured and held by the air bearing. The fly height exhibits some deviation about a given nominal fly height. As used herein, a vacuum port is any opening within a surface of air bearing 44 in fluid communication with a passage, such as a pipe, tube or other structure for the conveyance of a gas, and connected with or intended for connection to a vacuum source, such as a vacuum pump. Vacuum ports may be interconnected, such as through a common plenum disposed within air bearing 44, through a common plenum external to air bearing 44, or be individually supplied with a vacuum.

Air bearing 44 comprises a major surface 46, which is the surface closest to the adjacent glass sheet to be measured, comprising channels or grooves, and vacuum ports, as will be discussed in more detail below. For the purpose of clarity, reference to angular locations on major surface 46 will be made in reference to an outer circumference of the circular air bearing, with a position of 0 degrees being located at the top-most point of the air bearing, and increasing angular position relative to a center of the circular air bearing occurs in a clockwise rotation through 360 degrees.

Referring to FIG. 2, conveyor 48 may be used to transport a glass sheet in a direction of travel 50 along a predetermined path through apparatus 40 so that a measurement of the glass sheet may be made. For example, conveyor 48 may comprise an overhead rail equipped with a clamping mechanism 49 that travels along the rail and which also clamps to a top edge of the glass sheet to be measured. Preferably the clamping mechanism is configured to roll or slide along the rail. Moreover, conveyor 48 is preferably equipped with a drive mechanism that moves the clamping mechanism, and the glass sheet, along the rail assembly. For example, the rail assembly may be fitted with a driven chain or belt connected to the clamping mechanism, wherein a motor or other motive force is used to move the chain or belt, thereby causing the clamping mechanism, and therefore the glass sheet clamped by clamping mechanism 49, to traverse along the rail assembly and through apparatus 40. As used herein, the direction of travel 50 represents a forward movement of the glass sheet through apparatus 40. In addition, the terms upstream and downstream are used relative to direction of travel 50. That is, upstream is to be construed as a direction generally opposite to direction of travel 50, whereas downstream is to be construed as being in a direction generally the same as direction 50. However, it should be noted that upstream and downstream designations do not require that the direction referred to is identical, or exactly opposite the direction of travel 50. It is only required that the direction referred to has no vector component in the opposite direction. For example, an upstream direction has no downstream vector component. Additionally, upstream and downstream may be used to refer to a stationary position with respect to the moving glass sheet. In this respect, upstream refers to a position that encounters the moving glass sheet first in respect of another stationary position. Thus, the glass sheet traveling in direction of travel 50 may pass one fixed point or object before passing a subsequent point or object. The first-passed point or object is referred to as the upstream point or object relative to the subsequent point, whereas the subsequent point or object is the downstream point or object relative to the first-passed point.

Apparatus 40 further comprises a plurality of glass sheet stabilizing air knives comprising a first stabilizing air knife 52a positioned such that the first stabilizing air knife will be located opposite a first major surface of the glass sheet (where the first major surface of the glass sheet is the glass surface closest or adjacent to the air bearing), and a second stabilizing air knife 52b located opposite a second major surface of the glass sheet. Put more simply, one air knife is positioned adjacent to one side of the glass sheet while the other air knife is positioned adjacent to the other or opposite side of the glass sheet. Additional glass sheet stabilizing air knives 52a, 52b may be positioned such that they are opposite the first or second major surface of the glass sheet as needed. For example, FIGS. 2 and 3 depict four pair of stabilizing air knives arrayed in rows and column. Apparatus 40 may comprise additional, positioning air knives positioned upstream of air bearing 44, downstream of the air bearing and/or opposite the air bearing to assist in positioning the glass sheet relative to the air bearing, as described in more detail further below.

Apparatus 40 also comprises an edge guiding device 54 for guiding glass sheets into position for measurement. Edge guiding device 54 is located upstream of the stabilizing air knives relative to the travel direction of the glass sheet and functions to reduce or eliminate side-to-side sway of the glass sheet and to guide the glass sheet between the stabilizing air knives. In the embodiment shown in FIGS. 2 and 3 and as perhaps best shown in FIG. 4, edge guiding device 54 comprises a pair of guide arms 56a, 56b configured to form guide slot 58 for receiving the lower edge of the glass sheet. Preferably guide slot 58 is wedge or V-shaped, where a distance d between the guide arms at an inlet (upstream) end of guide slot 58 (relative to glass sheet direction of travel 50) where a glass sheet enters the guide slot is greater than a distance d' between guide arms 56a, 56b at an outlet (downstream) end of the guide slot. More simply put, the distance between the guide arms varies along a length of the guide slot and direction 50 such that the guide slot narrows as a glass sheet progresses through the guide slot, thereby forming a V-shaped slot that narrows in a direction toward air bearing

Figure 4:
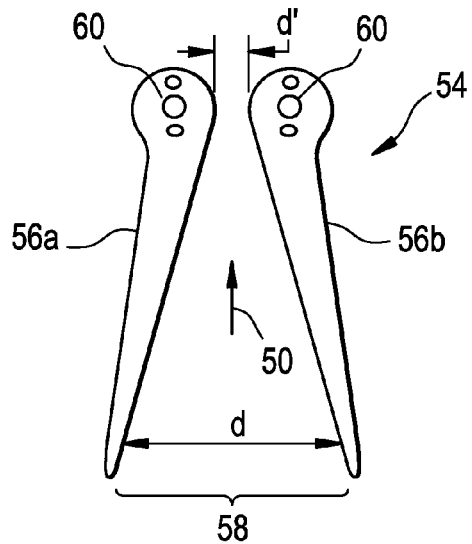
FIG. 4 is a top down view of an edge guiding device according to an embodiment of the present invention.

44. Preferably, as shown in the embodiment of FIG. 4, each guide arm may be rotatably mounted to frame 42 by axle pins or bolts that are inserted into a complimentary hole 60 in each guide arm and fasten to frame 42. Alternatively, each guide arm may comprise a pin that is fit within a complimentary hole in frame 42. Thus, the guide arms can be rotated to vary a shape of guide slot 58. Means for locking the guide arms is also preferably provided, thereby allowing each guide arm to be immobilized when a suitable slot shape is implemented. For example, the guide arms may be fitted with clamps or locking screws. In some embodiments, apparatus 40 may comprise a plurality of edge guiding devices 54. The width d of guide slot 58 should be sufficient to accommodate the largest anticipated side-to-side movement, or sway, of the glass sheet (where the glass sheet is rotating about clamping mechanism 49) to facilitate capture of the glass sheet. For example, if d is not sufficiently wide, a swaying glass sheet may not be captured within guide slot 58 but instead conveyed into contact with elements of apparatus 40, thereby potentially damaging the glass sheet or the apparatus. Width d will be dependent on the parameters of a particular process configuration. As described, width d' is smaller than width d, should be sufficiently large to prevent binding of the glass sheet as it travels through guide slot 58, but should also be sufficiently narrow that side-to-side sway is reduced or eliminated. Width d' is dependent, for example, on the thickness of the glass sheet and the magnitude of any curvature exhibited by the sheet. Alternatively, edge guiding device 54 may be a block of material comprising a slot machined into an upper surface of the block.

Figure 5:
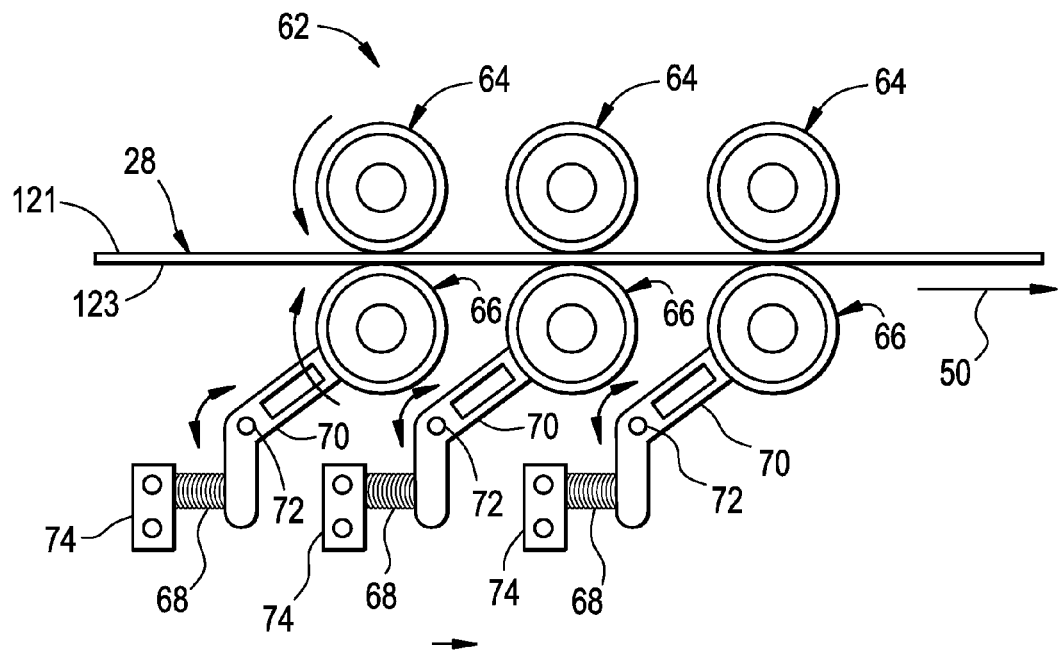
FIG. 5 is a top down view of an edge constraining device according to an embodiment of the present invention.

Apparatus 40 preferably also comprises an edge constraining device 62, best seen in FIG. 5, to hold the lower edge 63 of the glass sheet as the glass sheet is moving in the first direction 50 adjacent the air bearing. For example, edge constraining device 62 can be a plurality of guide rollers comprising one or more pairs of opposing rollers positioned along the path of the glass sheet as it traverses apparatus 40. In accordance with the embodiment of FIG. 5, each roller pair comprises a fixed position roller 64 and an opposing movable roller 66. The fixed roller of a roller pair is configured to be rotatable, but not otherwise movable. That is, while fixed position roller 64 can rotate about an axis of rotation of the roller, it is not adapted to translate or swing (describe an arc). On the other hand, the opposing movable roller 66 of the roller pair is configured to be both rotatable and to be movable (e.g. translatable) such that a distance between a fixed position roller 64 and an opposing movable roller 66 can vary. Preferably, movable roller 66 is urged toward fixed position roller 64, such as with a spring 68. As shown by FIG. 5, movable roller 66 is coupled to a pivot arm 70 that pivots about a pivot point 72. Spring 68 is compressed between pivot arm 70 and spring stop 74, whereby movable roller 66 is urged toward fixed position roller 64. A glass sheet 28 that is inserted between fixed position roller 64 and movable roller 66 causes movable roller 66 to rotate about pivot point 72 and describe a circular arc centered about pivot point 72. A simultaneous movement of pivot arm 70 against spring 68 further compresses spring 68. That is, the axis of rotation of movable roller 66 itself rotates about pivot point 72. Accordingly, movement of movable roller 66 away from fixed position roller 64 is resisted by the force exerted by spring 68 through pivot arm 70, and movable roller 66 is urged against glass sheet 28 so that glass sheet 28 is pinched between the fixed roller and the movable roller.

Figure 6:
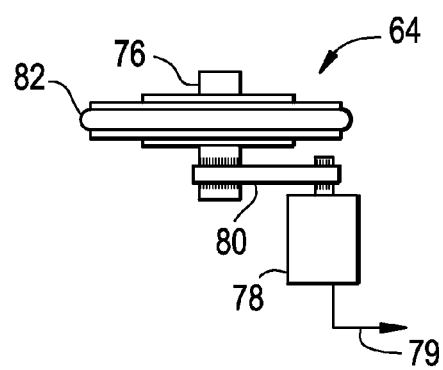
FIG. 6 is a side view of a roller of the edge constraining device of FIG. 5 showing the roller engaged with a rotary encoder.

To track progress of the glass sheet through apparatus 40, at least one roller of constraining device 62 may include a rotary encoder device to sense the rotational movement of the rotating roller and convert the rotational movement to an electrical signal. FIG. 6 depicts a side view of a fixed position roller 64 comprising roller axle 76 and rotary encoder 78 coupled to the roller through roller axle 76 and drive belt 80. Other methods of coupling rotary encoder 78 may be employed, as are known in the art. Rotary encoder 78 rotates as a ratio of the rotation of the roller and develops or modifies an electrical signal 79. The developed or modified electrical signal 79 from rotary encoder 78 may then be conveyed to a receiving computational device (not shown), where a linear movement of the glass sheet can be calculated using the rotational data from the rotary encoder. As best shown in FIG. 6, each fixed position roller 64 and each movable roller 66 comprises a resilient surface 82 to prevent damage resulting from contact between the roller and the glass sheet.

Figure 7:
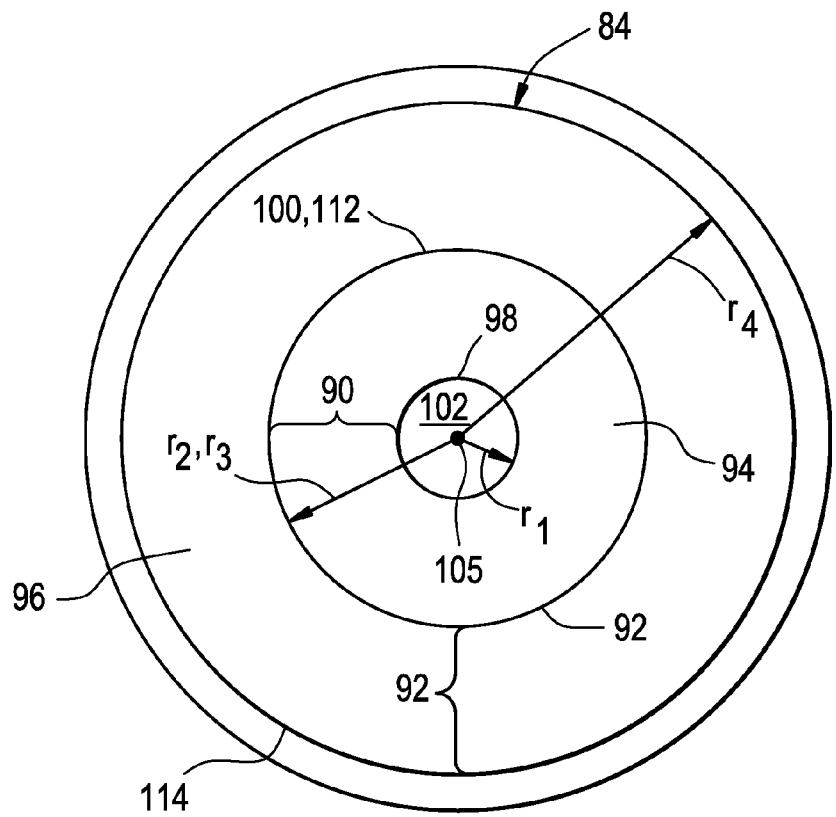
FIG. 7 is a simplified front view of an air bearing according to an embodiment of the present invention illustrating the inner porous body portion and the outer porous body portion.
Figure 8:
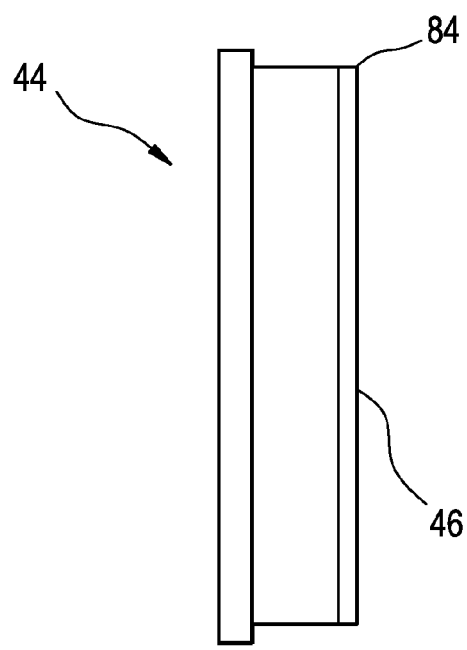
FIG. 8 is a side (edge) view of the air bearing of FIG. 7.
Figure 9:
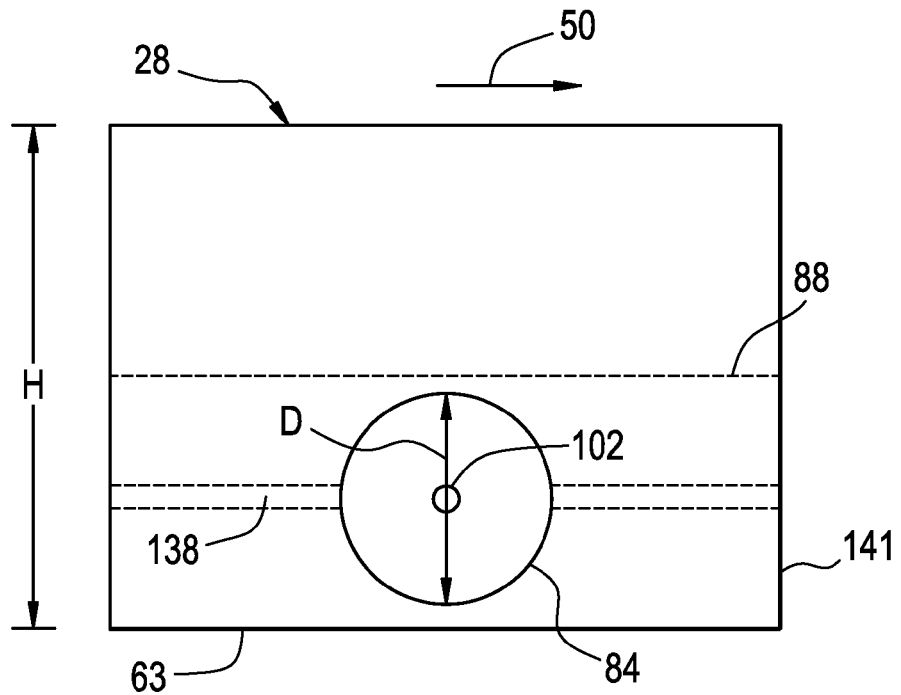
FIG. 9 is a front view of an air bearing according to an embodiment of the present invention shown in relation to a position of the air bearing relative to a glass sheet.

Referring now to FIGS. 7 and 8, air bearing 44 comprises a porous body 84 comprising generally planar major surface 46. As used herein porous means a rigid but sponge-like material in that it comprises millions of minute random channels through the thickness of the material resulting in a uniform distribution of holes at an external surface thereof, each hole almost insignificant by itself However, when the porous material is supplied with a gas under pressure the holes together supply a substantially uniform flow of air from a surface of the material. A suitable porous material in keeping with the present definition is graphite. Other materials, such as sintered metal powders may also be used, but the added risk of scratching the glass surface due to the hard abrasive nature of the metal argues for a softer material, such as graphite. As shown in FIG. 9, the overall height D of porous body 84 is typically no more than one half the height H of the glass sheet 28 to be measured (where dashed line 88 represents H/2), and preferably the height of porous body 84 is no greater than one third the height of the glass sheet, or less, where the height of the glass sheet is the dimension of the glass sheet in a vertical direction when the glass sheet is hanging vertically from conveyor 48. Moreover, as also shown in FIG. 9, it is preferable that during operation the air bearing is positioned adjacent only the bottom portion of the glass sheet. That is, the air bearing is preferably positioned so that porous body 84 is adjacent only the lower one half or less of the glass sheet, or a portion thereof. If porous body 84 is positioned high on the glass sheet (e.g. above dashed line 88), the glass sheet may be subject to undue stress resulting from the constraint placed on the glass sheet by both the conveyor clamping mechanism and the constraint applied by the air bearing. The resulting stress may break the glass sheet.

Returning to FIG. 7, porous body 84 is further divided into a first, or inner porous body portion 90 and a second, or outer porous body portion 92 disposed about the inner porous body portion. Accordingly, planar major surface 46 is divided into an inner planar surface 94 comprising inner porous body portion 90, and an outer planar surface 96 comprising outer porous body portion 92. Inner planar surface 94 and outer planar surface 96 may be coplanar.

Inner porous body portion 90 of air bearing 44 is annular in shape, having a circular inner circumference 98 defined at a radius $r_1$ from the center of the inner circumference and an outer circumference 100 defined at a radius $r_2$ from the center of the inner circumference. In addition, inner circumference 98 denotes the outer circumference of a passage 102 extending through air bearing 44. In a typical embodiment, passage 102 is in a range from about 3 cm to about 8 cm in diameter. However, passage 102 may be larger or smaller, depending on need and the nature of the measurement to be taken. Measurement device 104 (see FIG. 2) is located such that air bearing 44 is positioned between glass sheet 28 and measurement device 104 and so that an optical axis 105 of the measurement device extends through passage 102. Such a "through" measurement is beneficial that the plane of inspection (fixed by measurement device 104) and the plane of the glass are coplanar. Optical axis 105, may, for example, coincide with the center of inner circumference 98 as shown in FIG. 7. In other embodiments, measurement device 104 may be positioned so that glass sheet 28 is between measurement device 104 and air bearing 44. Nevertheless, measurement device 104 should still be positioned such that optical axis 105 of measurement device is aligned to pass through passage 102. However, in certain embodiments, passage 102 may be eliminated when the measurement is to be taken from the side of glass sheet 28 facing porous body 84 if reflection of light from porous body 84 does not affect the quality of, or otherwise interfere with, the particular measurement being performed. Optical axis 105 of measurement device 104 may be, for example, a laser beam emitted by the measurement device toward glass sheet 28.

Figure 10:
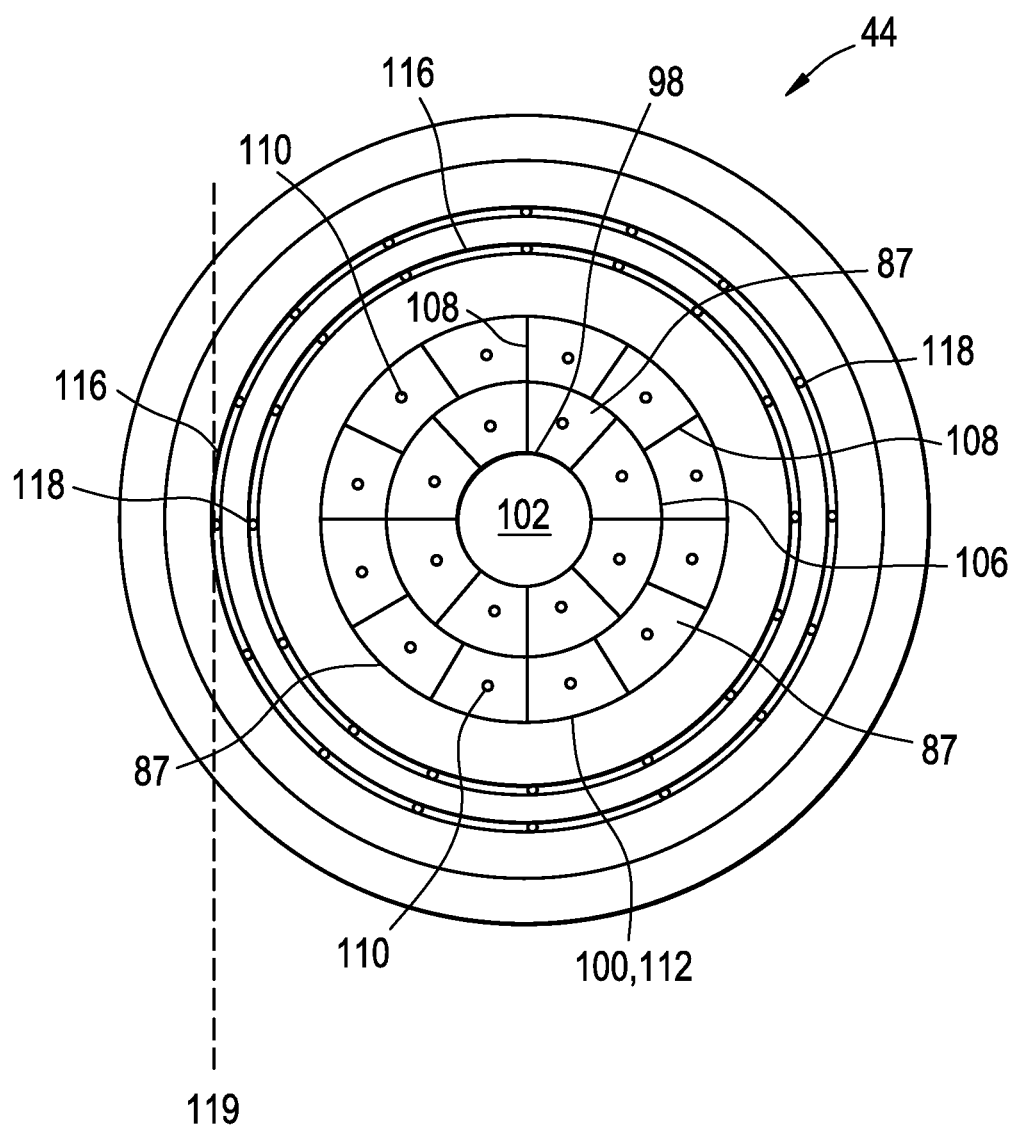
FIG. 10 is a detailed view of the air bearing of FIG. 7.

Referring now to FIG. 10, inner porous body portion 90 comprises at least one circular groove 106 concentric with inner circumference 98. Inner porous body portion 90 further comprises a plurality of grooves 108 extending radially on inner planar surface 94 and intersecting with circular groove 106. Radial grooves 108 are preferably arranged at periodic angular positions in a spoke-like fashion. Circular groove 106 and intersecting radial grooves 108 divide inner planar surface 94 into a plurality of sub-surfaces 87. Each sub-surface 87 comprises at least one vacuum port 110 in fluid communication with a vacuum source (not shown), as previously described.

Like inner porous body portion 90, outer porous body portion 92 of air bearing 44 is arcuate in shape, but need not possess a circular outer circumference. For example, outer porous body portion may be elliptical or oval in shape. Outer porous body portion 92 is disposed about inner porous body portion 90 and comprises a circular inner circumference 112 defined at a radius $r_3$ from the center of inner porous body portion 90 described above. In embodiments wherein outer porous body portion 92 comprises a circular outer circumference, i.e. circumference 114 shown in FIG. 7, outer circumference 114 is defined at a radius $r_4$ from the center of inner circumference 98. In some embodiments, $r_2=r_3$ and therefore inner circumference 112 of outer porous body portion 92 is the same as the outer circumference 100 of inner porous body portion 90.

Still in regard to FIG. 10, outer porous body portion 92 further comprises a plurality of continuous grooves 116 formed in outer planar surface 96. Each continuous groove 116 comprises a plurality of vacuum ports 118 extending through the porous body and connected to a vacuum source. Preferably, the plurality of vacuum ports 118 are arrayed periodically within each continuous groove 116 so that the angular displacement between vacuum ports disposed in a given continuous groove is equal. For example, within a given continuous groove 116, a vacuum port 118 may be positioned every 5 degrees, every 10 degrees or every 15 degrees around the groove. It is not necessary that the vacuum ports of one continuous groove 116 coincide angularly with the vacuum ports of another continuous groove 116. In some cases, particularly when the outer circumference of outer porous body portion 92 is circular, continuous grooves 116 are preferably circular and concentric.

Figure 11:
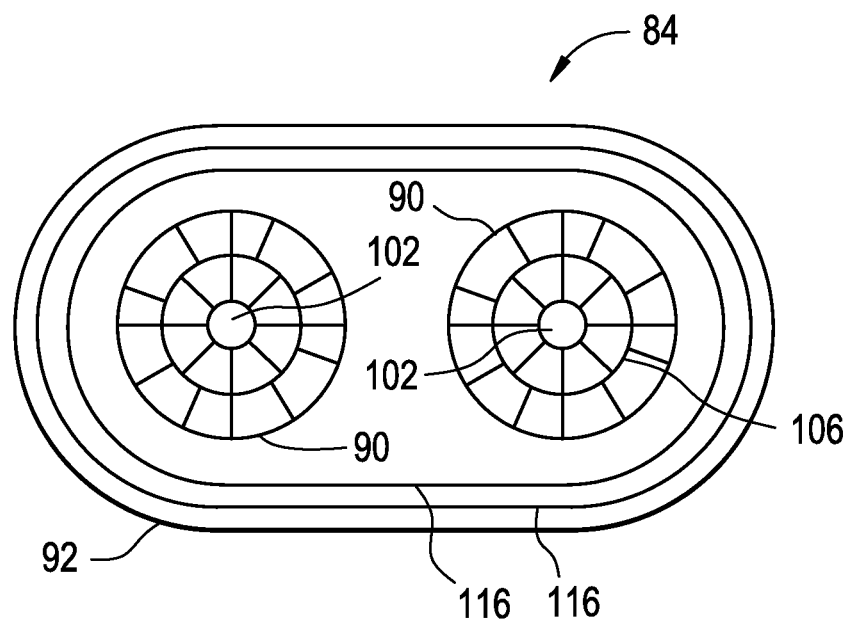
FIG. 11 is a frontal view of another embodiment of an air bearing wherein the air bearing comprises a plurality of inner piorous body portions.

In some embodiments, such as that depicted in FIG. 11, air bearing 44 may comprise a plurality of inner porous body portions 90 positioned within outer porous body portion 92, each inner porous body portion defining a passage 102. This can be particularly helpful when multiple measurements, for simultaneously determining multiple characteristics of the glass sheet, are to be taken and cannot be incorporated into a single measurement device.

Figure 12A:
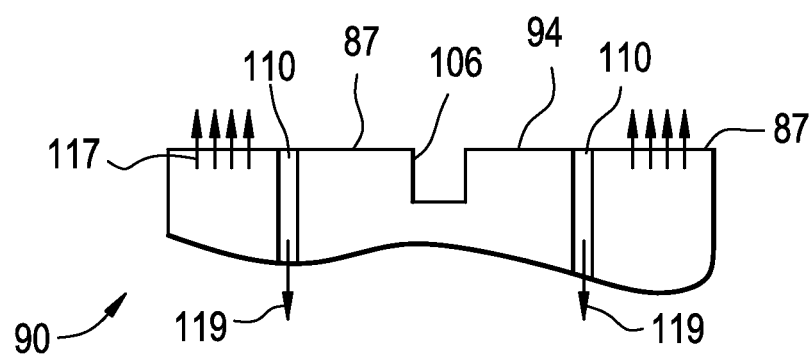
FIG. 12A is a cross sectional view of a portion of the inner porous body portion of the air bearing of FIG. 10.
Figure 12B:
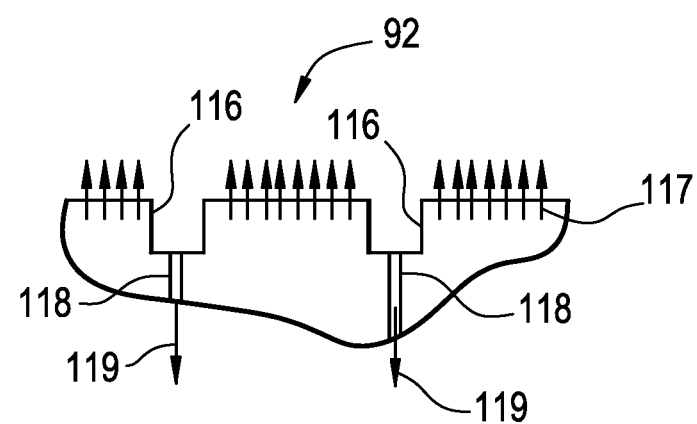
FIG. 12B is a cross sectional view of a portion of the outer porous body portion of the air bearing of FIG. 10.

The organization of grooves and vacuum ports can be better seen with the aid of FIGS. 12A and 12B, where FIG. 12A depicts a cross sectional view of a portion of inner porous body portion 90, and FIG. 12B depicts a cross sectional view of a portion of outer porous body portion 92. Both inner porous body portion 90 and outer porous body portion 92 are supplied with a pressurized gas, such as air, that issues from the planar surface of each porous body portion as represented by arrows 117. Together, the vacuum produced at the vacuum ports, depicted by arrows 119, and the air pressure produced over the planar surfaces of the porous body portions define two zones: a low precision capture zone adjacent outer planar surface 96 and a high precision capture zone coincident with inner planar surface 94. In the low precision capture zone the fly height of the glass sheet may be greater than the fly height of the glass sheet adjacent the high precision capture zone. A fly height of the glass sheet adjacent the low pressure capture zone can typically by in the range from about 40 μm to 60 μm, whereas the fly height of the glass sheet adjacent the high precision zone can typically be less than 40 μm.

As previously described, and in accordance with the embodiment of FIGS. 2 and 3, apparatus 40 comprises a plurality of stabilizing air knives 52a, 52b positioned upstream of air bearing 44 relative to the direction of travel 50 of glass sheet 28 through apparatus 40. The plurality of stabilizing air knives comprises a first stabilizing air knife 52a positioned such that the first stabilizing air knife will be located opposite first major surface 121 of glass sheet 28 (See FIG. 18), and a second stabilizing air knife 52b positioned such that the second stabilizing air knife will be located opposite second major surface 123 of glass sheet 28. First major surface 121 of glass sheet 28 is the surface of the glass sheet closest to porous body 84 when the glass sheet is adjacent to the air bearing, whereas second major surface 123 is the surface of glass sheet 28 farthest from porous body 84 under the same condition. The flow of air from the at least first and second stabilizing air knives of the plurality of stabilizing air knives stabilizes lateral (side-to-side) motion of the glass sheet in conjunction with the at least one edge guiding device 54 as the glass sheet enters the space between the stabilizing air knives, and helps to flatten the sheet. More simply put, even though the glass sheet may be impeded from lateral movement at the upper and lower edges of the glass sheet by conveyor clamping mechanism 49 at the upper edge of the glass sheet and edge guiding device 54 at the lower edge of the glass sheet, the glass sheet may still deform in a direction perpendicular to the general plane of the glass sheet, much the way a cloth sail can billow in the wind. This is because the glass sheet can be very large, and very thin, giving the glass sheet an increased flexibility when compared to much thicker glass plates. For example, a thickness of the glass sheet can be less than 1 mm.

Each stabilizing air knife is oriented such that the flow of air from each stabilizing air knife is directed toward the glass sheet in a downward direction, generally toward the bottom of the glass sheet, to create a more laminar flow of air over the major surfaces of the glass sheet and prevent turbulence and subsequent buffeting of the glass sheet. Preferably, although not necessarily, first and second stabilizing air knives 52a, 52b are arranged to mirror each other across the glass sheet. For example, in some embodiments, such as the embodiment of FIGS. 2 and 3, the plurality of stabilizing air knives are preferably arranged as multiple pairs of partially or substantially opposing air knives. That is, while the air knives may be directly opposing each other, this is not necessary, and there may be some offset between such "pairs" of air knives. However, in some embodiments the offset may be substantial. The number of stabilizing air knives is process dependent, and will depend, for example, on the transport speed of the glass sheet, the size and weight of the glass sheet and the amount of side-to-side sway exhibited by a glass sheet in a particular manufacturing process line. Similarly, the exact placement of an air knife on one side of the glass sheet compared to the placement of another air knife on the other side of the glass sheet will depend on the particular process conditions of the installation.

Figure 13:
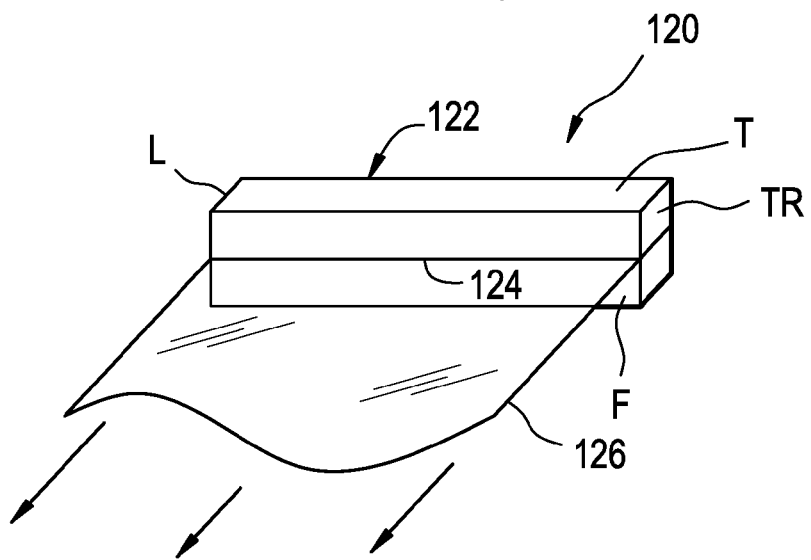
FIG. 13 is a perspective view of an exemplary linear stabilizing air bearing according to the present invention, illustrating the flow of air from the elongated nozzle in a planar fashion.

FIG. 13 illustrates an exemplary stabilizing air knife (here designated generally by reference numeral 120) comprising a generally elongate body 122 having an elongate orifice 124 from which a flow 126 of air issues. For simplicity, the air knife is represented by a longitudinally extended rectangular block. Each elongate orifice 124 is in fluid communication with a source of pressurized gas that enters the air knife through a coupling. The air knife may include an interior plenum in fluid communication with orifice 124. As air is quite satisfactory as a gas, being both plentiful and essentially free, the remaining description will assume an air-based air knife. Each elongate body 122 is arranged such that a direction of flow of the air emitted from each elongate orifice 124 is at a downward angle relative to a reference horizontal plane. Each stabilizing air knife, as represented by exemplary stabilizing air knife 120, includes a forward or leading end L and a rearward or trailing end TR relative to the direction of travel 50 of the glass sheet. That is, the leading end of the air knife is farther upstream than the trailing end of the air knife. When the air knife is supplied with pressurized air, the air issues from elongate orifice 124 at a high velocity. While the air issuing from the elongate orifice 124 may eventually begin to diverge after leaving the stabilizing air knife, for at least a short distance, on the order of several 10s of millimeters, the air issues from the air knife as a substantially laminar flow 126 that can be approximated by a plane. Exemplary stabilizing air knife 120 further comprises a top surface T.

In the event that the stabilizing air knives are arranged in a complimentary opposing relationship (i.e. are mirrored across an intervening vertical plane between the stabilizing air knives that is parallel with air bearing major surface 46), a distance between the leading ends of an opposing stabilizing air knife pair may be greater than a distance between the trailing ends of the opposing stabilizing air knife pair. That is, the distance between the opposing air knives narrows as the glass sheet progresses between the air knives in a manner similar to the narrowing of guide slot 58.

In still another optional characteristic, each stabilizing air knife of the plurality of stabilizing air knives may be oriented such that the trailing end of each stabilizing air knife is higher (or lower) than the leading end of the stabilizing air knife. In some embodiments each stabilizing air knife can be straight (i.e. rectangular shaped) similar to exemplary air knife 120. However, preferably each stabilizing air knife is arcuate and may comprises a circular arc. Suitable stabilizing air knives of either the straight (linear) variety, or the arcuate design, can be obtained, for example, through Exair Corporation located in Cincinnati, Ohio, USA.

Figure 14:
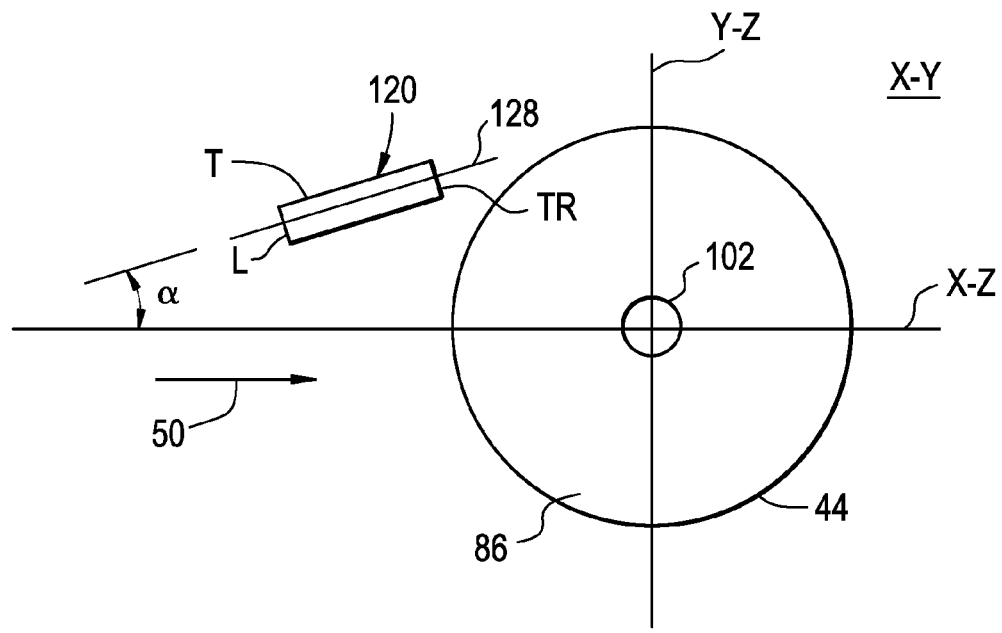
FIG. 14 is a front view of the air bearing of FIG. 7 illustrating downward angle of an exemplary stabilizing air knife.
Figure 15:
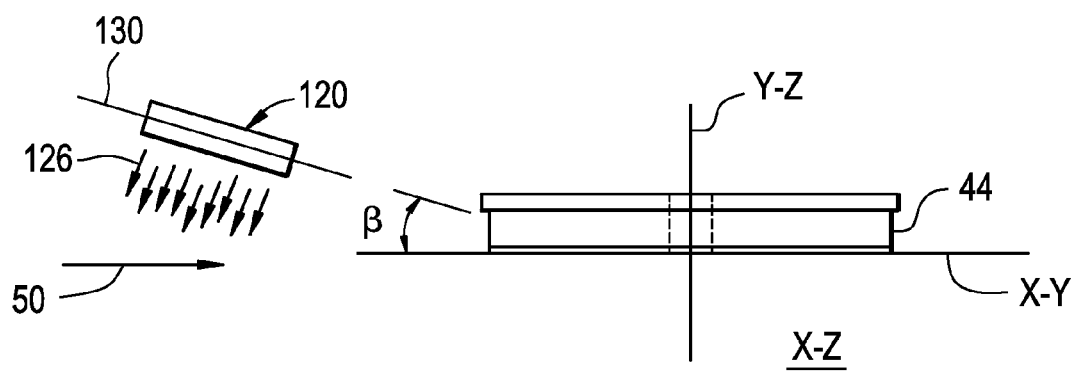
FIG. 15 is a top down view of the air bearing of FIG. 7 illustrating a sideways angle of an exemplary stabilizing air knife.
Figure 16:
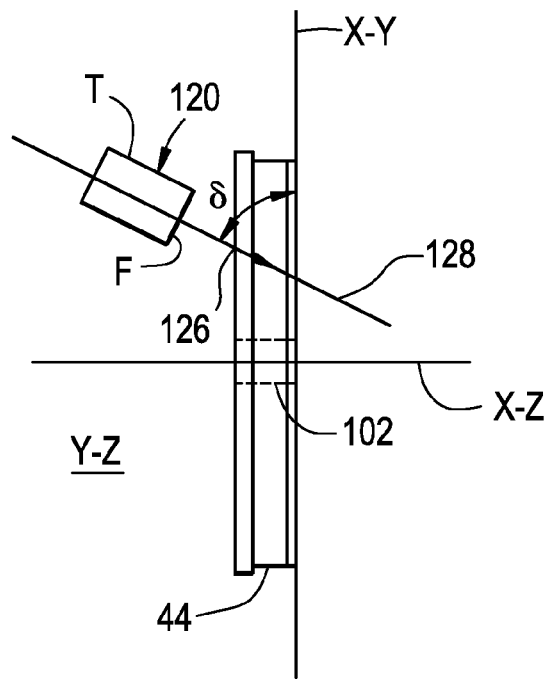
FIG. 16 is a side (edge) view of the air bearing of FIG. 7 illustrating a downward of a flow of air issuing from an exemplary stabilizing air knife.

How each stabilizing air knife may be spatially oriented can be visualized in more detail with the following description and aid of FIGS. 14-16. The orientation of a body in three-dimensional space requires a frame of reference, and a means of orienting the body in that frame of reference. FIG. 14 shows a vertical X-Y plane coplanar with major surface 46 of porous body 84. For the purpose of further discussion, this X-Y plane forms one plane in a three-dimensional Cartesian coordinate reference frame. This X-Y plane lies within the plane of the page on which FIG. 14 is depicted. A second vertical plane, seen from an edge thereof in FIG. 14, forms a Y-Z plane of the Cartesian coordinate system where the Z direction extends perpendicular to and therefore out of the page. The Y-Z plane is perpendicular to the X-Y plane. A third, X-Z plane, also seen from an edge thereof in FIG. 14, is arranged to be perpendicular to both the X-Y and Y-Z planes. For the purpose of further discussion, and unless otherwise described, the origin of the Cartesian coordinate system formed by the three planes X-Y, Y-Z and X-Z described above lies at the center of inner porous body portion 90, and this Cartesian coordinate system will be used to describe the orientation of the air knives in three dimensional space.

FIGS. 14-16 depict the three optional orientations of exemplary stabilizing air knife 120, and by extension therefore the optional spatial orientations of each stabilizing air knife, shown separately to aid in visualizing the orientations. FIG. 14 depicts an outline of air bearing 44 as seen looking at major surface 46 and indicating the direction of travel 50 of the glass sheet. Exemplary stabilizing air knife 120 exhibits a downward pitch or incline in that the leading end L of the stabilizing air knife is lower than the trailing end TR of the stabilizing air knife relative to the horizontal X-Z plane. To wit, plane 128 representing the flow of air from the exemplary stabilizing air knife makes an angle $\alpha$ with the X-Z plane.

FIG. 15 shows a second view looking down on an edge of air bearing 44 and shows an edge of the Y-Z plane and an edge of the X-Y plane. The X-Z plane is perpendicular to both the X-Y plane and the Y-Z plane. Plane 130 is a plane longitudinally bisecting top surface T of exemplary stabilizing air knife 120 and is perpendicular to plane 126 representing the flow of air from the air knife. In accordance with FIG. 15, exemplary stabilizing air knife 120 may be angled relative to the vertical X-Y plane such that a non-zero angle $\beta$ is formed between plane 130 and the X-Y plane.

FIG. 16 shows a third view looking down on an edge of air bearing 44 and shows an edge of the X-Z plane and an edge of the X-Y plane. The Y-Z plane is perpendicular to both the X-Y plane and the X-Z plane. FIG. 16 illustrates exemplary stabilizing air knife 120 from an end thereof oriented such that the flow of air exiting the air knife is directed downward (from a reference horizontal flow, e.g. parallel with the horizontal X-Z plane) and the plane of the air flow makes an acute angle $\delta$ with the X-Y plane rather than being directed, for example, perpendicular to the glass sheet. Preferably, $\delta$ is in the range from about 15 degrees to about 75 degrees, preferably in the range from about 25 degrees to about 65 degrees, and more preferably in the range from about 35 degrees to about 55 degrees. In one embodiment, the angle of the air flow is about 45 degrees relative to the vertical X-Y plane. It should be noted that the preferred direction for the air flow is downward, since a low positioning of the air bearing relative to the glass sheet gives the lower portion of the glass sheet more stiffness to resist buckling of the glass sheet due to the air flow. However, in some embodiments, an upward air flow may be preferred depending on process conditions and the particular implementation, e.g. positioning, of the air bearing.

The preceding description presented three optional orientations of an exemplary stabilizing air knife 120. Each stabilizing air knife of the plurality of stabilizing air knives may exhibit at least one orientation of the three optional orientations described above in respect of a representative exemplary stabilizing air knife. For example, each stabilizing air knife of the plurality of stabilizing air knives may exhaust air such that the direction of air flow from the air knives is generally downward (i.e. the flow vector comprises a vertical vector component). Thus, for example, two stabilizing air knives located on opposite sides of the glass sheet and wherein the stabilizing air knives are mirror images of each other, will form a generally V-shaped flow of air, with the "V" pointed downward.

Similarly, each stabilizing air knife of the plurality of stabilizing air knives may be oriented such that a leading end of each stabilizing air knife is farther from the glass sheet than a trailing end. Thus, for example, two stabilizing air knives located on opposite sides of the glass sheet and wherein the stabilizing air knives are mirror images of each other, will form a generally V-shaped flow of air, with the "V" pointed downstream toward the air bearing. This provides more lateral clearance for a glass sheet exhibiting lateral movement as it enters between the air knives. It also provides for a more gradual application of the curtain of air flowing from the stabilizing air knives, as the pressure on the glass sheet from the flow of air from the leading end of each stabilizing air knife becomes less than the pressure of the air on the glass sheet adjacent the trailing end of a stabilizing air knife.

Similarly, each stabilizing air knife of the plurality of stabilizing air knives may be oriented such that a leading end of each stabilizing air knife is lower relative to a horizontal reference plane (for example, the X-Z plane) than a trailing end. It can be said that the stabilizing air knives are pitched or inclined forward to flatten out any shape distortion (e.g. bow) in the sheet.

Each stabilizing air knife of the plurality of air knives may exhibit one or more of the orientations described above. In some embodiments, one or more of the stabilizing air knives may simultaneously exhibit all three orientations.

In addition to the stabilizing air knives and as seen in FIG. 3, for example, a first positioning air knife 132 may be placed between the stabilizing air knives (52a, 52b) and air bearing 44 such that the flow 126 of air from the first positioning air knife impinges on first major surface 121 of the glass sheet adjacent to the leading edge of the air bearing. For example, first positioning air knife 132 may be located at an approximately 270 degree position on air bearing 44. The pressure produced on the glass sheet as it passes adjacent to first positioning air knife 132 forces the glass sheet away from the air bearing. This prevents contact between the leading or forward edge of the glass sheet as it approaches the air bearing until the glass sheet can be "captured" by the air bearing.

A second positioning air knife 134 may be positioned such that air from the second positioning air knife impinges on second major surface 123 of the glass sheet. The effect of the air from the second positioning air knife is to force the glass sheet in a direction toward the air bearing, thus bringing the glass sheet closer to the air bearing and allowing the air bearing to capture the glass sheet. Initial capture of the glass sheet is accomplished by the combination of pressure and vacuum produced by the outer porous body portion.

A third positioning air knife 136 may be positioned downstream from the air bearing and positioned such that air emitted by the third positioning air knife is directed against first major surface 121 of the glass sheet. The air pressure produced by third positioning air knife 136 forces the glass sheet away from the air bearing surface near the downstream edge of the air bearing and thereby prevents contact between the glass sheet and the air bearing as the glass sheet moves past and disengages from the air bearing. Each positioning air knife 132, 134 and 136 may be similar in design to a stabilizing air knife. For example, each stabilizing air knife and each positioning air knife may be of the arcuate design or of the linear design. Preferably, the air emitted from each of the positioning air knives 132, 134 and 136 is directed against the glass sheet such that the curtain of gas from each positioning air knife forms an angle less than 90 degrees but greater than zero with the surface of the glass sheet, for example, greater than 25 degrees and less than 75 degrees, and preferably greater than 35 degrees and less than 65 degrees, preferably greater than 35 degrees and less than 55 degrees. For example, a typical embodiment may orient each positioning air knife so that the flow of air impinges on the glass sheet at an angle of about 45 degrees. An angle of impingement less than 90 degrees produces less turbulence at the surface of the glass sheet than, for example, air flow that is perpendicular to the glass sheet.

The overall effect of the various non-contact glass sheet handling components of apparatus 40 is to provide gradually increasing constraint on the glass sheet to prepare the glass sheet for measurement. As previously noted, in some instances the glass sheet is conveyed vertically, secured only at the top of the glass sheet by the conveyor clamp. As the glass sheet may be very thin, equal to or less than 1 mm, and in some cases equal to or less than 0.7 mm, or in other cases equal to or less than 0.3 mm, the glass may easily exhibit lateral movement by swaying side-to-side (i.e. rotate about the fixed carrier contact points), or deform by various bending modes (as used herein, a bending mode is analogous to a vibrational mode). The glass can also be offset due to carrier-to-carrier variations in the clamping and the position of the carrier on the conveyor. As well, the glass can be bowed vertically.

Various glass sheet handling components of apparatus 40 serve to reduce or eliminate these motions, and fixed shapes, such as bow. Accordingly, operation of apparatus 40 may proceed along the following steps.

A glass sheet 28 is attached to conveyor 48 by one or more clamping mechanisms 49 that grip the glass sheet along a top edge of the glass sheet translate the glass sheet through apparatus 40. Glass sheet 28 is thereby hanging from the one or more clamping mechanisms, and supported only by the one or more clamping mechanisms clamped to the glass sheet along a top portion of the glass sheet. The lower edge 63 of the glass sheet is unsupported and initially capable of lateral movement, i.e. a swaying movement, before entering apparatus 40. In addition to lateral movement, the glass sheet may also exhibit flexure or bending. For example, the sheet may bend cylindrically or hyperbolically or be saddle shaped, dome shaped, or exhibit other bending modes, or combinations thereof.

As glass sheet 28 nears apparatus 40, the glass sheet is guided by at least one edge guiding device 54 that engages with lower edge 63 of the glass sheet and guides the leading edge of the glass sheet between stabilizing air knives 52a, 52b. Lower edge 63 forms part of the "non-quality" portion of the glass sheet and may later be removed. The at least one edge guiding device 54 minimizes or eliminates side-to-side swaying. Testing has shown embodiments of edge guiding device 54 as disclosed herein can reduce the lateral motion of swaying from a maximum displacement of +/−75 mm to less than +/−10 mm. However, while the at least one edge guiding device 54 may provide excellent control of lateral movement of the lower edge of the glass sheet, the glass sheet is only substantially constrained at the top and bottom edges, and is still capable of exhibiting various bending modes and fixed shapes within the body of the glass sheet. To minimize or eliminate this additional movement or shape of the glass sheet before moving adjacent to porous body 84, stabilizing air knives are employed.

The flow of air emitted by opposing stabilizing air knives, preferably in a downward direction, may further reduce lateral movement of the glass sheet to eliminate side-to-side swaying of the glass sheet, and in particular, reduces or eliminates bending modes. In effect, the stabilizing air knives help stiffen the glass sheet by at least reducing the magnitude of the bending and in some cases by eliminating one or more bending modes. The number and positioning of the stabilizing air knives is dependent on such factors as the size of the glass sheet, the thickness of the glass sheet, the density of the glass, and the traverse speed of the glass sheet through apparatus 40.

As the glass sheet passes between the stabilizing air knives, lower edge 63 of the glass sheet may be guided by one or more additional edge guiding devices 54 to further guide and stabilize the glass sheet. For example, in some embodiments, multiple edge guiding devices may be employed; with a first edge guiding device employed upstream of the stabilizing air knives and a second edge guiding device positioned just prior to the edge constraining device 62.

Figure 17:
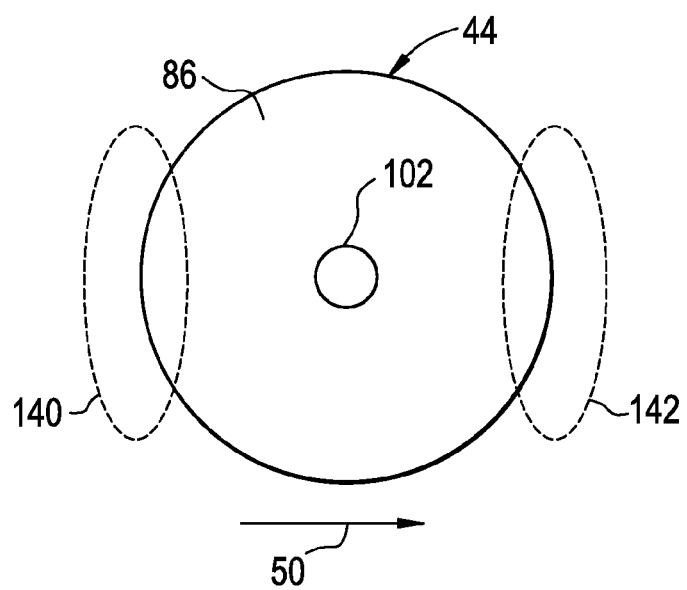
FIG. 17 is a front view of the air bearing of FIG. 7 depicting the leading and trailing edges of the air bearing in relation to the direction of travel of the glass sheet.

As the glass sheet approaches air bearing 44, optional first positioning air knife 132 may be used to direct a flow of air at first major surface 121 of the glass sheet. The force of the air from first positioning air knife 132 against first major surface 121 of glass sheet 28 pushes the glass sheet away from the leading edge 140 (see FIG. 17, and more particularly region A of FIG. 18) of air bearing 44 and prevents contact between leading edge 140 of the air bearing and leading edge 141 of glass sheet 28 as the glass sheet comes under the influence of outer porous body portion 92 of air bearing 44. Contact between the glass sheet and the air bearing may result in damage, in some instances catastrophic, to the glass sheet.

As the glass sheet continues to move forward along direction of travel 50, the glass sheet passes over a first vacuum port 118 of outer porous body portion 92. Preferably, air bearing 44 is positioned such that a vacuum port 118 positioned within the outer-most groove of outer porous body portion 92 is positioned so that as the glass sheet advances, it first moves adjacent to this single vacuum port 118. Referring to FIG. 10, this first vacuum port 118 is the vacuum port farthest to the left and lying in the outermost continuous groove 116 in FIG. 8, and intersecting with dashed line 119. The effect of this initial encounter with a first vacuum port 118 is that leading edge 141 of glass sheet 28 is moved closer to outer porous body portion 92. That is, while the region of the glass sheet adjacent leading edge 141 of the air bearing is being pushed away from the air bearing leading edge, a region of the glass sheet adjacent the first vacuum port 118 is forced in the direction of outer porous body portion 92. By bringing at least this portion of the glass sheet adjacent the first vacuum port 118 close to the air bearing, that portion of the glass sheet is captured by the outer porous body portion 92 of air bearing 44. Continued forward movement of the glass sheet brings the glass sheet adjacent to additional vacuum ports 118 of outer porous body portion 92. Within a short distance of the leading edge of glass sheet 28 passing adjacent to the additional outer porous body portion vacuum ports 118, sufficient force is exerted on the glass sheet as a result of air flow at the outer porous body portion that a substantial portion of the glass sheet adjacent to air bearing 44 exhibits a substantially uniform fly height relative to the first major surface of the air bearing.

Again, as the glass sheet continues to move forward adjacent to inner porous body portion 90, the flatness and rigidity of the glass sheet increases, particularly those portions of glass sheet 28 directly adjacent to inner porous body portion 90, such that measurements may be taken by measurement device 104 through passage 102.

It should be recalled that measurements of the glass sheet, such as interferometric measurements for the purpose of determining surface topography of glass sheet 28, may be taken simultaneously with the forward movement of the glass sheet (i.e. in direction 50). As the glass sheet trailing edge passes inner porous body portion 90, and then outer porous body portion 92, the constraint to the glass sheet applied by the action of the air bearing 44 decreases, and the air pressure from optional positioning air knife 136 is able to overcome the holding force applied by air bearing 44 such that the trailing edge of the glass sheet is pushed away from the air bearing so that contact between the glass sheet and the air bearing does not occur. The pressurized air supplied to inner porous body portion 90, and the vacuum, may be adjusted, for example, such that the fly height of the glass sheet is maintained to have a deviation less than about 30 μm (+/−15 μm).

From the preceding it can be seen that a region of the glass sheet is opposite passage 102 as the glass sheet moves past air bearing 44. Thus, passage 102, while defining a circular measurement zone, "sweeps" a rectangular measurement region 138 of the glass sheet as shown in FIG. 9. Measurement device 104 makes continuous measurements of the glass within this rectangular region. For example, measurement device 104 may be an interferometer for making surface topography measurements of the glass sheet within the rectangular measurement zone, or measurement device 104 may make measurement of the thickness of the glass sheet.

Eventually, continued forward travel of the glass sheet along direction of travel 50 brings the trailing edge 142 of the glass sheet past air bearing 44. Air issuing from third positioning air knife 136 and impinging on first major surface 121 of the glass sheet forces the region of the glass sheet proximate the trailing edge 142 of air bearing 44 away from the air bearing, thereby avoiding contact between the glass sheet and the air bearing surface. This becomes particularly beneficial as the surface area of the glass sheet under the influence of the stabilizing air knives and/or the air bearing decreases.

Figure 18:
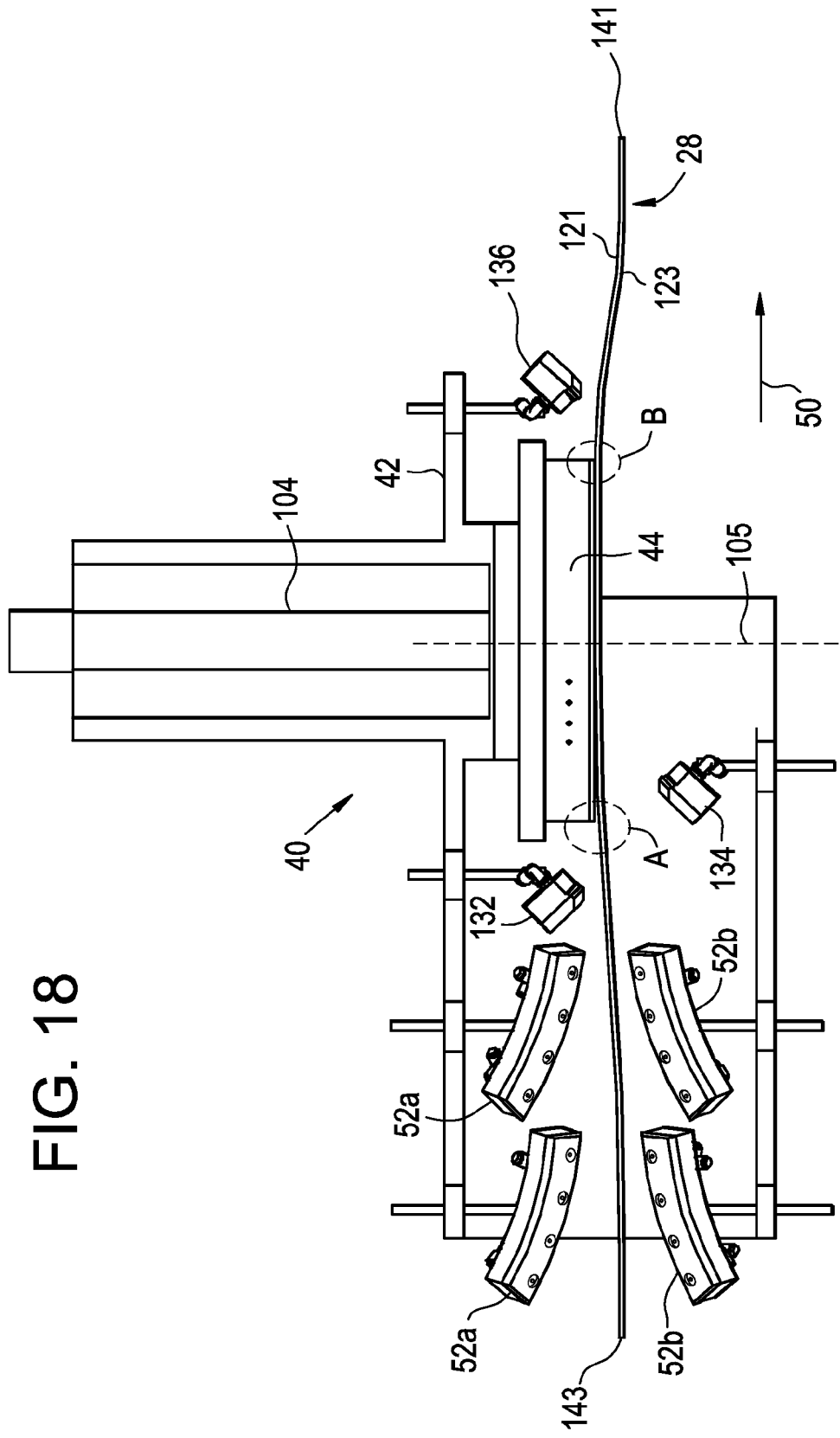
FIG. 18 is a top down view of the apparatus of FIG. 2 showing the curvature produced in a glass sheet by the apparatus.

The result of the forces supplied by positioning air knives 132, 134 and 136 can be seen with the aid of FIG. 18, showing apparatus 40 in a top view and depicting glass sheet 28. The effect of positioning air knives 132 and 136 can be seen in the regions designated by reference numerals A and B and circled by dashed lines. Indeed, it can be seen from FIG. 18 that the glass sheet overall takes on a non-planar aspect until the glass sheet is fully engaged by the air bearing, at which point the glass sheet adjacent to the air bearing is fully flat, although it should be noted that the only region where planarity is needed is where a measurement is occurring, e.g. in the center of the measurement zone.

Figure 19:
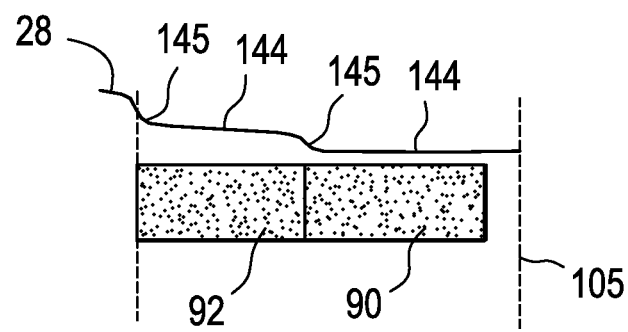
FIG. 19 is a cross sectional side view of a portion of the air bearing of FIG. 17 showing details of the curvature of the glass sheet adjacent to the air bearing.

FIG. 19 depicts an edge view of the glass sheet extending from the center of the inner porous body portion to the leading edge of the air bearing and shows in more detail the shape of the glass sheet over the air bearing. It should be kept in mind that the illustration of FIG. 19 is greatly exaggerated, as the deflections involved are on the order of tens of microns. As shown, the glass sheet can be divided into several distinct regions separated by equally distinct boundaries, giving the portion of the glass sheet over the air bearing the appearance of a series of relatively flat plateaus 144 separated by S-shaped boundary features 145, wherein the fly height of the plateaus decrease in a direction toward the center of the inner porous body portion (e.g. the area defined by passage 102).

Figure 20:
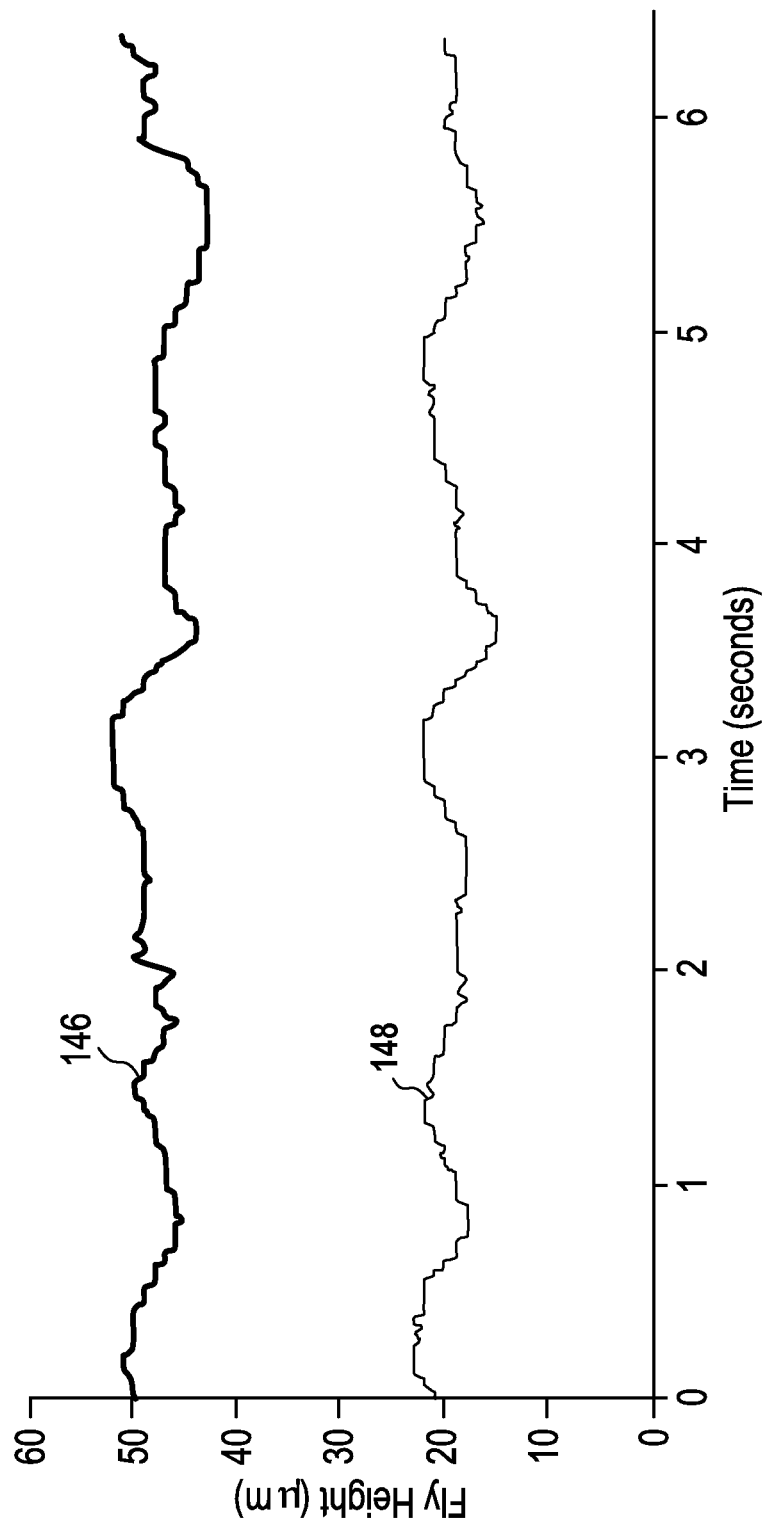
FIG. 20 is a graph of fly height vs. time for two locations on the glass sheet as the glass sheet traveled at a speed of 100 mm/s, and illustrating the stability of the glass sheet position (i.e. fly height consistency).

FIG. 20 is a graph of measured fly heights for a glass sheet traveling through an embodiment of apparatus 40 with a travel speed of 100 mm/s measured at two different locations for a glass sheet. The vertical "Y" axis represents fly height in microns while the horizontal "X" axis represents time. The measurements were taken at a predetermined frequency (250 sec$^{-1}$) for a given location. Thus, the graph of FIG. 20 can be used to obtain the fly height at a predetermined position over time as the glass sheet traverses adjacent to the air bearing. The glass sheet had an initial side-to-side sway of +/−75 mm from a nominal centerline position. Each stabilizing air knife directed air against the glass sheet at a downward angle of 45 degrees. The inner porous body portion of the air bearing was supplied with air at a pressure of 20 psi to 60 psi at a flow rate of 0.63+/−0.25 CFM, while the outer porous body portion was supplied with air at a pressure of 40 to 85 psi and a flow rate of 0.96+/−0.35 CFM. The fly height of the glass sheet over the circular measurement zone defined by passage 102 was nominally 28 μm with a variation of less than +/−2.5 μm. Curve 146 of FIG. 20 shows the fly height of the glass sheet at the outer circumference of inner porous body member 90 at a position of approximately 210 degrees, with the glass sheet traveling at a speed of 100 mm/s, while curve 148 of FIG. 20 depicts the fly height at the center of the inner porous body portion (i.e. the center of passage 102). The curves for travel of the glass sheet are particularly telling for showing the stability of the fly height at both locations of the glass sheet—the measurement location at the outer circumference of the outer porous body portion and the measurement location over the center of the porous body. While the nominal fly height differs between the two regions, being significantly greater for the outer porous body location than for the center of the porous body, the fly height at both locations is surprisingly stable, showing a variation less than about ±2.5 microns.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. An apparatus for characterizing glass sheets as the glass sheets move past the apparatus comprising:
   a conveyor configured to support a glass sheet in a vertical orientation and to move the vertically oriented glass sheet in a direction of travel past the apparatus;
   an air bearing comprising an annular inner porous body portion, and an outer porous body portion disposed about the inner porous body portion, the inner porous body portion defining a central passage extending through a thickness of the air bearing, wherein the outer porous body portion and inner porous body portion are positioned to be adjacent a major surface of the glass sheet as said glass sheet moves past the apparatus; and
   a plurality of stabilizing air knives positioned to be adjacent opposing major surfaces of the glass sheet as said glass sheet moves past the apparatus and disposed upstream of the air bearing relative to the direction of travel of the glass sheets, wherein the air knives are oriented such that a flow of air from each air knife is directed toward the respective major surface of the glass sheet; and
   a measurement device to measure at least one attribute of the glass sheet, the measurement device being aligned with the central passage of the air bearing.

2. The apparatus according to claim 1, wherein the inner porous body portion comprises a circular groove in a surface thereof, and a plurality of radial grooves intersect the circular groove.

3. The apparatus according to claim 2, wherein the surface of the inner porous body portion comprises a vacuum port.

4. The apparatus according to claim 1, wherein the outer porous body portion comprises a plurality of continuous grooves, each continuous groove comprising a plurality of vacuum ports.

5. The apparatus according to claim 1, wherein an outer circumference of the outer porous body portion is arcuate.

6. The apparatus according to claim 1, wherein the air bearing comprises a plurality of inner porous body portions.

7. The apparatus according to claim 1, wherein the measurement device is configured to measure the at least one attribute through the central passage.

8. The apparatus according to claim 1, wherein the stabilizing air knives are oriented such that a flow of air from the stabilizing air knives is angled in a downward direction relative to the glass sheets.

9. The apparatus according to claim 1, further comprising an edge guiding device comprising guide arms arranged to form a "V"-shaped slot therebetween.

10. The apparatus according to claim 1, wherein the plurality of stabilizing air knives are arcuate in shape.

11. The apparatus according to claim 1, further comprising an air knife positioned downstream of the air bearing.

\* \* \* \* \*